US00PP13375P2

(12) United States Plant Patent
Dümmen

(10) Patent No.: US PP13,375 P2
(45) Date of Patent: Dec. 17, 2002

(54) PETUNIA PLANT NAMED 'DUESURBLUSKY'

(75) Inventor: Marga Dümmen, Rheinberg (DE)

(73) Assignee: Dümmen JungpflanzenKulturen, Rheinberg (DE)

( * ) Notice: Subject to any disclaimer, the term of this patent is extended or adjusted under 35 U.S.C. 154(b) by 0 days.

(21) Appl. No.: 10/104,367

(22) Filed: Mar. 22, 2002

(51) Int. Cl.[7] ..... A01H 5/00
(52) U.S. Cl. ..... Plt./356
(58) Field of Search ..... Plt./356

(56) References Cited

PUBLICATIONS

Hit on 'Duesurblusky', UPOV–ROM Plant Variety Database, GTI Jouve Retrieval software, 2001/05.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Petunia plant named 'Duesurblusky', characterized by its upright and outwardly spreading plant habit; freely basal branching; and single flowers that are purple in color.

1 Drawing Sheet

BOTANICAL CLASSIFICATION/CULTIVAR DESIGNATION

*Petunia×hybrida* cultivar Duesurblusky.

BACKGROUND OF THE INVENTION

The present Invention relates to a new and distinct cultivar of Petunia plant, botanically known as *Petunia×hybrida*, and hereinafter referred to by the cultivar name Duesurblusky.

The new Petunia is a product of a planned breeding program conducted by the Inventor in Rheinberg, Germany. The objective of the breeding program is to create new freely branching Petunias with large flowers and attractive flower coloration.

The new Petunia originated from a cross pollination made by the Inventor in 1997 of a proprietary Petunia selection identified as code number E-19-2, not patented, as the female, or seed parent, with a proprietary Petunia selection identified as code number S-19-3, not patented, as the male, or pollen parent. The new Petunia was selected as a single plant from the resulting progeny by the Inventor in Rheinberg, Germany in 1998, on the basis of its attractive flower color.

Asexual reproduction of the new cultivar by terminal vegetative cuttings taken in Rheinberg, Germany since 1999, has shown that the unique features of this new Petunia are stable and reproduced true to type in successive generations.

SUMMARY OF THE INVENTION

Plants of the cultivar Duesurblusky have not been observed under all possible environmental conditions. The phenotype may vary somewhat with variations in environment such as temperature and light intensity without, however, any variance in genotype.

The following traits have been repeatedly observed and are determined to be the unique characteristics of 'Duesurblusky'. These characteristics in combination distinguish 'Duesurblusky' as a new and distinct cultivar:

1. Upright and outwardly spreading plant habit.
2. Freely basal branching.
3. Single fowers that are purple in color.

Compared to plants of the female parent, the selection E-19-2, plants of the new Petunia differ in flower color. Compared to plants of the male parent, the selection S-19-3, plants of the new Petunia have smaller leaves, smaller flowers and differ in flower color.

Plants of the new Petunia can be compared to plants of the cultivar Surfinia Blue, not patented. In side-by-side comparisons conducted in Rheinerg, Germany, plants of the new Petunia differed from plants of the cultivar Surfinia Blue in the following characteristics:

1. Plants of the new Petunia were shorter than plants of the cultivar Surfinia Blue.
2. Plants of the new Petunia had smaller leaves than plants of the cultivar Surfinia Blue.
3. Plants of the new Petunia had smaller flowers than plants of the cultivar Surfinia Blue.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ slightly from the color values cited in the detailed botanical description which accurately describe the colors of the new Petunia. The photograph comprises a top perpective view of typical flowers and leaves of 'Duesurblusky'.

DETAILED BOTANICAL DESCRIPTION

The cultivar Duesurblusky has not been observed under all possible environmental conditions. The phenotype may vary somewhat with variations in environment such as temperature and light intensity without, however, any variance in genotype.

The aforementioned photographs, following observations and measurements describe plants grown during the spring in Rheinberg, Germany, under commercial practice in a glass-covered greenhouse. Plants were about 16 weeks from cuttings and were grown in containers. During the production of the plants, day and night temperatures averaged 18° C. and light levels were about 4,500 lux. Plants were pinched once about three weeks afer planting.

In the following description, color references are made to The Royal Horticultural Society Colour Chart, 1995 Edition, except where general terms of ordinary dictionary significance are used.

Botanical classification: *Petunia×hybrida* cultivar Duesurblusky.

Parentage:

*Female parent.*—Proprietary *Petunia×hybrida* selection identified as code number E-19-2, not patented.

*Male parent.*—Proprietary *Petunia×hybrida* selection identified as code number S-19-3, not patented.

Propagation:

*Type cutting.*—Terminal vegetative cuttings.

*Time to initiate roots.*—Summer: About 7 days at 20° C. Winter: About 10 days at 20° C.

*Time to develop roots.*—Summer: About 21 days at 20° C. Winter: About 28 days at 20° C.

*Root description.*—Fine, fibrous, white in color.

*Rooting habit.*—Freely branching.

Plant description:

*Form.*—Annual flowering plant; indeterminate; upright and outwardly spreading; eventually cascading. Moderately vigorous.

*Usage.*—Appropriate for hanging baskets, window boxes, patio containers and landscape applications.

*Plant height.*—About 26 cm.

*Plant diameter.*—About 25 cm.

*Branching habit.*—Freely basal branching with about five to six lateral branches per plant.

*Lateral branches.*—Length: About 29 cm. Diameter: About 4 mm. Internode length: About 1.7 cm. Texture: Pubescent. Color: 144B.

*Folige description.*—Arrangement: Before flowering, alternate; after flowering, opposite; simple. Quantity per lateral branch: About 16. Length: About 5 cm. Width: About 3 cm. Shape: Roughly spatulate. Apex: Obtuse. Base: Attenuate: Margin: Entire. Texture, upper and lower surfaces: Pubescent; leathery. Venation pattern: Pinnate. Color: Young and fully expanded foliage, upper surface: 137A. Young and fully expanded foliage, lower surface: 137C. Venation, upper and lower surfaces: 144B. Petiole length: About 7 mm. Petiole diameter: About 3 mm. Petiole color: 144B.

Flower description:

*Flower type and habit.*—Single salverform flowers; flowers face mostly upward or outward; axillary; about four flowers and flower buds per lateral branch.

*Natural flowering season.*—Long day responsive; spring until frost in the autumn; flowering continuous. Plants start flowering about nine weeks after planting. Flowers persistent.

*Flower longevity on the plant.*—About 4 days; flowers persistent.

*Fragrance.*—None detected.

*Flower size.*—Diameter: About 5.5 cm. Tube length: About 3.1 cm. Throat diameter, distal end: About 1 cm. Tube diameter, proximal end: About 3 mm.

*Flower buds.*—Length: About 3.7 cm. Diameter: About 5 mm. Shape: Ovoid. Color: 59A.

*Corolla.*—Quantity/arrangement: Five fused petals; funnelform. Petal length from throat: About 2.5 cm. Petal width: About 2.4 cm. Petal shape: Roughly spatulate. Petal apex: Obtuse. Petal margin: Entire; slightly ruffled. Petal texture, upper and lower surfaces: Smooth, velvety. Petal color: When opening, upper surface: 83A. When opening, lower surface: 86C. Fully opened, upper surface: 83B; flower color does not fade with subsequent development. Fully opened, lower surface: 86C. Flower throat (inside): 103A. Flower tube (outside): 59A. Venation, upper petal surface: 93A. Venation, lower petal surface: 144A. Venation, throat: 93A. Venation, tube: 144.

*Sepals.*—Arrangement/appearance: Single whorl of five sepals fused at base, star-shaped. Length: About 1 cm. Width: About 2.5 mm. Shape: Strap-like; elongate. Apex: Rounded. Margin: Entire. Texture, upper and lower surfaces: Pubescent. Color: Upper surface: 137B. Lower surface: 137C.

*Peduncles.*—Length: About 2 cm. Width: About 1.25 mm. Angle: Erect to slightly bent. Strength: Moderately strong. Texture: Pubescent. Color: 144B.

*Reproductive organs.*—Stamens: Quantity per flower: About five. Anther shape: Ovoid. Anther length: About 2.5 mm. Anther color: 92B. Pollen amount: Abundant. Pollen color: 122B. Pistils: Quantity per flower: One. Pistil length: About 2.8 cm. Style length: About 2.2 cm. Style color: 144C. Stigma shape: Rounded. Stigma color: 143A. Ovary color: 144B.

*Seed/fruit.*—Seed nor fruit production has not been observed.

Disease/pest resistance: Plants of the new Petunia have not been noted to be resistant to pathogens or pests common to Petunia.

Temperature tolerance: Plants of the new Petunia have been observed to tolerate temperatures from 2 to 38° C.

It is claimed:

1. A new and distinct cultivar of Petunia plant named 'Duesurblusky', as illustrated and described.

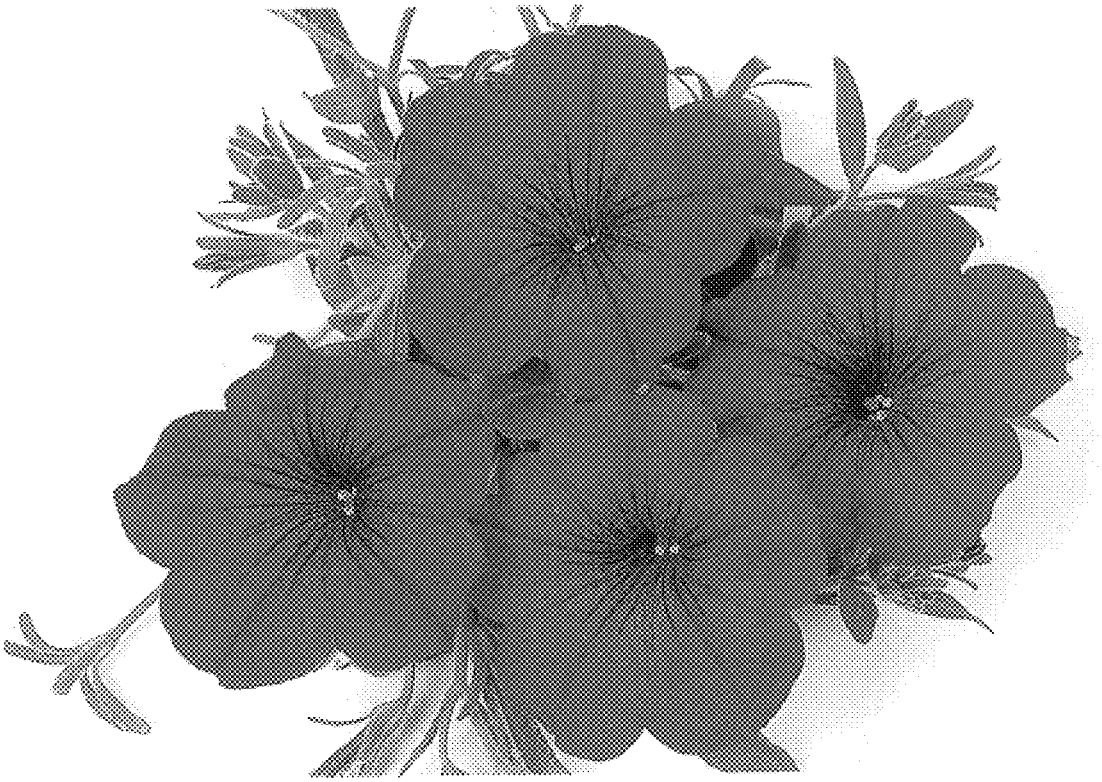

* * * * *